(12) United States Patent
Savage et al.

(10) Patent No.: US 6,670,159 B1
(45) Date of Patent: Dec. 30, 2003

(54) PREPARING MONOMERIC METAL ION CHELATOR CONTAINING DIACETYL GLYCINE GROUP LINKED TO PROTEINACEOUS MOLECULE

(75) Inventors: M. Dean Savage, Rockford, IL (US); Laura L. Sykaluk, Rockford, IL (US)

(73) Assignee: Pierce Biotechnology, Inc., Rockford, IL (US)

( * ) Notice: Subject to any disclaimer, the term of this patent is extended or adjusted under 35 U.S.C. 154(b) by 0 days.

(21) Appl. No.: 09/915,214

(22) Filed: Jul. 25, 2001

Related U.S. Application Data

(63) Continuation of application No. 09/386,633, filed on Aug. 31, 1999, now abandoned, which is a continuation-in-part of application No. 09/002,225, filed on Dec. 31, 1997, now abandoned.

(51) Int. Cl.⁷ .................. C12N 9/08; C12N 11/06; C12N 9/14; C07K 17/06; C08H 1/00
(52) U.S. Cl. .................. 435/192; 435/21; 435/28; 435/177; 435/180; 435/181; 435/195; 530/402; 530/413; 530/812; 530/815; 530/816
(58) Field of Search ................. 435/188, 174, 435/177, 180, 181, 192, 21, 28; 530/402, 413, 811, 812, 815, 816; 562/572

(56) References Cited

U.S. PATENT DOCUMENTS 5,266,686 A * 11/1993 Sorensen ............... 530/413
5,439,829 A * 8/1995 Anderson et al. ........... 436/518

OTHER PUBLICATIONS

Hermanson, et. al., Immobilized Affinity Ligand Techniques, Academic Press, Inc. N.Y., 1994, pp. 81–83.*

* cited by examiner

Primary Examiner—David M. Naff

(57) ABSTRACT

A precursor for the construction of chelated metal conjugates which demonstrate improved assay performance and utility in minimizing non-specific binding while maintaining specificity for target molecules is disclosed. The precursor has tridentate functionality towards multivalent ions such as iron and nickel and contains a diacetyl glycine group covalently linked via an amide to a molecule such as a proteinaceous molecule providing a primary amide group for amide bond formation. The precursor is preferably prepared in monomeric form by reacting nitrilotriacetic acid or a salt thereof in an aqueous medium at an alkaline pH of at least 8 with a proteinaceous molecule containing a primary amine group in the presence of a carbodiimide. The proteinaceous molecule may be bovine serum albumin or an enzyme such as alkaline phosphatase or horseradish peroxidase.

15 Claims, 8 Drawing Sheets

PREPARING MONOMERIC METAL ION CHELATOR CONTAINING DIACETYL GLYCINE GROUP LINKED TO PROTEINACEOUS MOLECULE

RELATED APPLICATION

This application is a continuation of application Ser. No. 09/386,633, filed Aug. 31, 1999, now abandoned, which is a continuation-in-part of application Ser. No. 09/002,225, filed Dec. 31, 1997, now abandoned.

FIELD OF INVENTION

The present inventions relates to metal ion affinity interactions with target molecules and, more particularly, to improvements thereof whereby non-specific interactions with non-target molecules can be diminished.

BACKGROUND OF INVENTION

Affinity binding interaction based on the used of a chelated metal have been widely used due to the propensity of certain metals to preferably bind to given functional groups on target molecules such as proteins, peptides, and like compounds. Immobilized metal-ion chromatography, for example, has been used with a variety of different metals. Phosphorylated target molecules have been purified using columns containing immobilized ferric ions. Polyhistidine tagged fusion proteins nave been purified using columns containing immobilized divalent nickel. Peroxidase and biotin probes containing chelated metals have also been used for polyhistidine tagged fusion protein detection and in connection with immunoassays.

It is recognized that in metal-ion chromatography, the chelating functionality used to immobilize the metal to construct the chelator-metal conjugate is important. With iron, iminodiacetic acid functionality has been used due to its tight binding characteristics with ferric ions. With nickel, as well with many other less used metal ions, the nitrilotriacetic acid tetradentate functionality has been used in both column and probe formats due to its tight binding characteristics with these metal ions.

A Problem often encountered in metal ion affinity interactions is that of nonspecific binding, whereby the constructed chelator-metal ion conjugate, typically immobilized on a support or bound to a detection moiety such as an enzyme, e.g., a peroxidase, binds to non-target molecules as well as target molecules. Binding to non-target molecules can result in decreased sensitivity, nigh background, and overall poor assay performance.

DETAILED DESCRIPTION OF THE INVENTION INCLUDING PREFERRED EMBODIMENTS THEREOF

Figure 1:
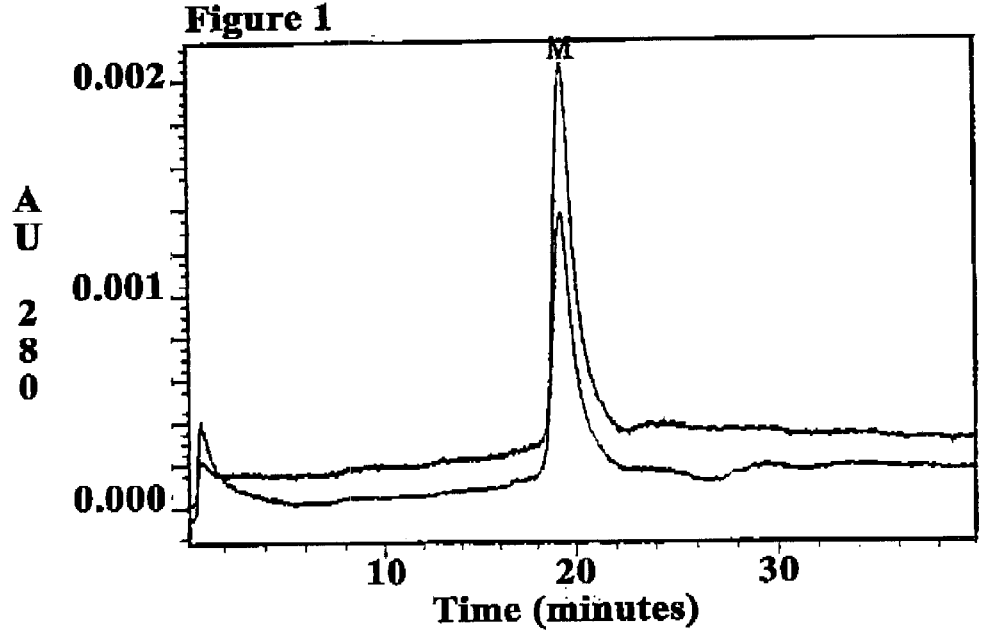
FIG. 1. depicts a sizing profile of chelate peroxidase precursor prepared at alkaline pH. M denotes monomeric form. Profile was monitored at two wavelengths, 405 and 280 nm.

In accordance with the present invention, there is provided a precursor for the construction of chelated metal ion conjugates which demonstrate improved assay performance and utility in minimizing non-specific binding while maintaining specificity for target molecules. The present invention provides a chelator having tridentate chelator functionality towards multivalent metal ions, said precursor containing a diacetyl glycine group covalently linked via an amide bond to a molecule providing a primary amine group for said amide bond formation. The precursor can be represented by the following structure:

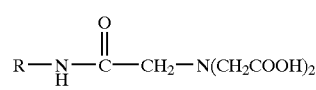

Formula I wherein R is a molecule providing a primary amine group, which group, as shown, provides the amide nitrogen of the amide bond. R can be, For example, a molecule allowing for detection such as an enzyme, fluorescent label, biotin, or other detectable moieties. Particularly useful enzymes are considered to be horseradish peroxidase (HRP), alkaline phosphatase, beta-galactosidase, and glucose oxidase. In addition to R being a detectable moiety, R can also be a molecule that serves as a carrier for the chelating moiety to enable subsequent adaptation of the constructed conjugate for uses in applications other than detection. Such uses include separation, attachment, and purification of target molecules. Accordingly, R can be, or example, proteinaceous molecules such as bovine serum albumin or casein as well as other molecules which have been derivatized to contain a functional primary amine group such as an oligonucleotide, carbohydrate, or conventional organic molecules.

In accordance with further aspects of the invention, a composition of matter is provided which contains the foregoing precursor in substantially monomeric form and chelated metal conjugates and compositions thereof prepared using the precursor.

Yet a further aspect of the present invention resides in the method of preparing the precursor in a manner which minimizes the formation of polymeric forms, and, to this end, a method provided which involves reacting, in an aqueous medium at alkaline pH in the presence of a carbodiimide, a nitrilotriacetic acid or salt thereof with a molecule containing a primary amine group to form an amide bond.

A still further aspect of this invention is to provide a method for improving an assay by diminishing non-specific binding of a chelated conjugate by a chemical treatment method which involves the use of amino acid modification reagents to block the non-target binding sites or the conjugate.

In further keeping with the invention sent forth herein, an acceptor surface is provided which includes a solid phase having noncovalently adhered thereto a chemically modified protein. The protein is chemically modified to provide a means for modulating, that is increasing or decreasing, the acceptance of the solid phase or a foreign substance.

Thus in accordance with the foregoing paragraph, the invention also provides an acceptor surface containing a solid phase have noncovalently linked thereto a chemically modified protein. The chemical modification of the protein adhered to the solid chase surface provides means for modulating the acceptance of the solid phase or a foreign substance. The chemically modified protein can be represented by the following formulas:

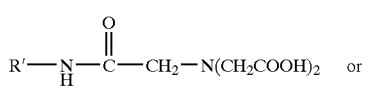

Formula II

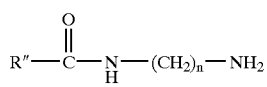

Formula III

Referring to the above Formulas II and III, R' and R" are the residues of the parent proteins after a free primary amine group has been reacted with a chelating moiety to form the chemically modified protein (Formula II) or free carboxyl group has been reacted with a diamine to form the chemically modified protein (Formula III).

As is evident the chemically modified protein represented by Formula II corresponds to the precursor represented as Formula I wherein R is a proteinaceous molecule. As to diamines useful in the preparation of Formula III modified proteins, ethylenediamine is preferred though other diamines having up to 6 carbon atoms are also considered to be useful.

Formation the chemically modified proteins represented by Formula III can be accomplished by known techniques, typically involving carbodiimide-mediated reaction of the protein with a diamine. A particularly useful protein so modified is cationized bovine serum albumin (cBSA). This protein, wherein the free carboxyl groups of the parent protein are modified to contain contain cationic aminoethylamide derivatives not normally found on the native protein, is commercially available and is prepared using ethylenediamine in a carbodiimide reaction with the parent protein. An acceptor surface having this modified protein adhered thereto is particularly useful in those instances where the solid chase would otherwise accept an unwanted foreign substance, such as a non-target (crossreactive) binding partner. Example IX illustrates the usefulness of preformed cBSA as an appropriate blocking agent for detection of protein with iron-activated HRP and example X illustrates the usefulness of in-situ formation of Formula III to limit non-target binding of iron-activated HRP in a microplate assay.

The precursor of the present invention represented by Formula I can be prepared by the carbodiimide-mediated condensation reaction between a primary amine group of a molecule (R as set forth above) and a single carboxylic acid group or nitrilotriacetic acid (NTA), the resulting amide bond linking together the two moieties containing theses respective groups. A useful carbodiimide is 1-ethyl-3-[3-dimethylaminopropyl]carbodiimide hydrochloride (EDC). The condensation reaction resulting in the preparation of the tridentate chelator used as the precursor in chelate formation can be readily accomplished in an aqueous medium at room temperature, the reaction generally continuing for several hours. Suitable aqueous mediums are those compatible with preservation of physiological integrity of the constituents. An example is a 2-(N-morphilino)ethanesulfonic acid (MES) buffer. After preparation, the precursor can be recovered free of contaminants by gel filtration utilizing a "Sephadex" column or other methods.

In accordance with an aspect of the invention, the condensation reaction forming a precursor is accomplished in an alkaline solution. To this end, the reaction occurs at a solution pH of at least 8 and preferably at least 9, e.g., a pH of 9–10. By forming the precursor at alkaline pH, the formation of polymerized byproducts, e.g., dimers and trimers, is suppressed; the product formed being substantially, i.e., at least 75% by weight, and preferably, at least 95% by weight, the monomeric form of the precursor.

To obtain an alkaline reaction medium for preparation of the precursor, it is convenient to use the trisodium salt of NTA due to its strong alkalinity in aqueous solution. An alternative is to adjust the pH of the reaction medium to alkaline pH values prior to proceeding with the reaction. When prepared under alkaline conditions, isolation and recovery of the precursor can be readily accomplished as stated above by gel filtration. Alternatively, if an order to obtain substantially monomeric precursor if an acidic reaction medium is utilized yielding both monomeric and polymeric species, then the monomeric form can be isolated and recovered by conventional purification methods such as gel filtration, ion exchange, etc.

Once obtained the precursor can be used to prepare metal-activated conjugates by well known techniques. Typically, a solution of a salt of the metal is added to a solution of the precursor and the metal is allowed to bind at room temperature to the tridentate chelating functionality. Reaction conditions, such as pH and buffer composition, are selected which are favorable to promote binding of the metal to the precursor and to avoid adverse consequences such as precipitation or the metal salt or loss of integrity of the molecule identified as R in Formula I. The metal activated conjugate from the reaction mixture may be suitable for direct use, or can be further purified by conventional methods such as gel filtration, if an excess of metal salt is used to activate precursor.

While iron, copper, and nickel are the most commonly used metals in metal affinity interactions, a variety or other metals for specific purposes can be employed. Examples include, among others, cobalt, and zinc.

The following examples illustrate the present invention. As used therein all parts and percentages are by weight unless indicated.

EXAMPLE I

This Example Illustrates the preparation of a chelator precursor wherein the molecule, R, containing the amine group is horseradish peroxidase (HRP).

To 48 mg HRP (MW≅40,000), 78.54 μl 0.1 MES, pH 5.5, was added followed by additions of 508 μl nitrilotriacetic acid, trisodium salt solution, pH 9.84, (prepared by dissolving NTA salt to 260 mg/ml in 0.1 M MES, pH 5.5, with no subsequent pH adjustment) and 613.46 μl EDC solution (prepared by dissolving EDC to 150 mg/ml in 0.1 M MES, pH 5.5 with no subsequent pH adjustment). The resulting pH of this reaction mixture was alkaline, approximately pH 9–10.

The solution was allowed to react for 2 hours at room temperature followed by desalting with a Sephadex G-25 column with 0.1 M MES, pH 5.5.

In comparison, the above described condensation reaction was carried out at typical acidic EDC reaction conditions, pH 5–6, by adjusting the reaction mixture pH prior to proceeding with the reaction.

Figure 2:
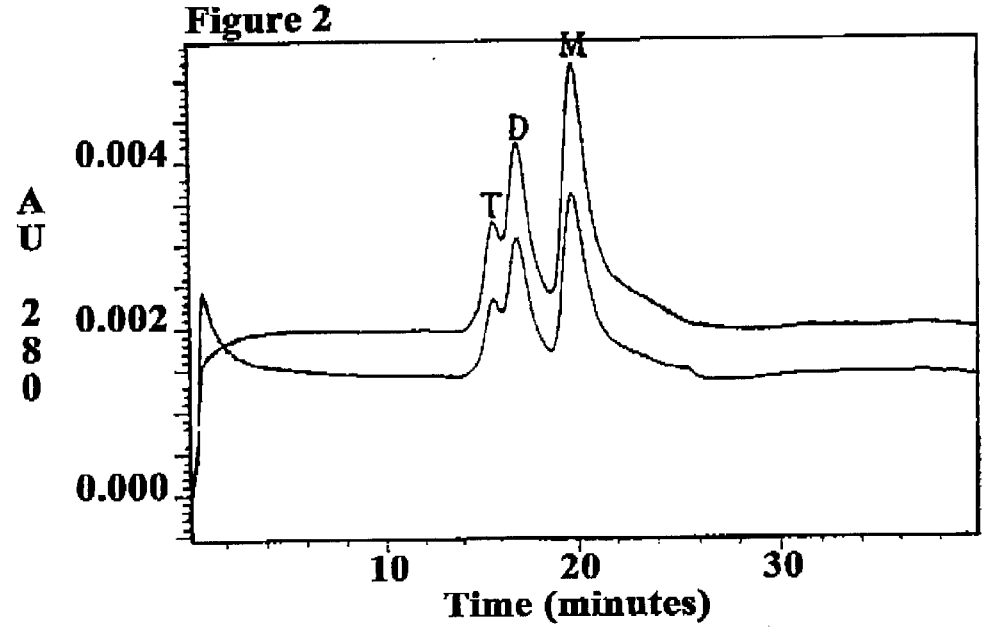
FIG. 2. depicts a sizing profile of chelate peroxidase precursor prepared using acidic pH reaction conditions typical for carbodiimide reactions. M denotes monomeric form; D denotes dimeric form; T denotes trimeric form. Profile was monitored at two wavelengths, 405 and 280 nm.

Investigation of molecular differences of the precursors was carried out using a sizing column (Waters PW-300) run in 50 mM phosphate buffer, pH 7.2. These results are shown in FIGS. 1 and 2. When prepared at normal EDC reaction pH values, (FIG. 2) the resulting chelating precursor was polymeric and contained peroxidase monomers, dimers, and trimers. However, when the reaction pH was carried out at alkaline pH, (FIG. 1), the resulting precursor was substantially all monomer. In turn, as shown in the following Table 1, metal-charged chelate conjugates (see Example II) prepared from the monomeric precursor, gave, in use, low assay background compared with conjugates similarly prepared from the precursor represented in FIG. 2.

The following Table I presents an illustration of comparative assay performance of the monomeric versus the polymeric chelate conjugates using the iron-charged peroxidase chelate in an assay to detect a phosphate containing peptide. The assay was conducted similarly to that described in Example XI.

TABLE 1

| Preparation | Dilution | Assay Background | Assay Signal/Noise Ratio |
|---|---|---|---|
| Monomeric | 3X | 0.093 | 11.26 |
|  | 1X | 0.075 | 10.44 |
| Polymeric | 2X | 0.151 | 7.63 |
|  | 1X | 0.164 | 6.93 |

As shown in Table 1, the monomeric chelate conjugate exhibited substantial improvement in assay performance as compared to the use of the polymeric chelate conjugate. The use of monomeric precursor not only decreased assay background, but also resulted in improved assay signal/noise ratios. Attempts to improve the performance of the polymeric chelate conjugate by dilution of the conjugate did not improve performance. Accordingly, the pH of the reaction during formation or the chelate precursor is important in achieving improved performance in metal binding affinity interactions; the monomeric form achieved at alkaline pH being decidedly preferred for use.

EXAMPLE II

This Example illustrates the preparation or iron and nickel activated chelate conjugates using the precursor prepared in Example I.

$FeCl_3 \cdot 6H_2O$ or nickel chloride was dissolved in 0.1 MES, pH 5–5.5 and added to the chelate precursor prepared in Example I at an eight fold molar excess based on a molecular weight of HRP of 40,000. Metal was allowed to bind to the precursor for 15 minutes at room temperature and the conjugates so formed subsequently used for probes in detection assays. With the use of an 8 fold molar excess, no further purification was required; equivalent results could be obtained with or without an optional gel filtration step. An eight fold molar excess was considered optimum based on assay performance when various metal loading concentration were tested.

EXAMPLE III

This Example illustrates the use of the nickel activated conjugate prepared in Example II as a probe for the detection of polyhistidine tagged fusion (PHT) proteins and the comparison of the conjugate so prepared with alternate probes.

Insect Sf9 cells were infected with recombinant baculovirus expressing rat peroxisome proliferator-activated receptor (pA), rat retinoid x receptor (pB) and human thyroid hormone receptor (pC). All proteins were tagged with six consecutive histidine residues. Three days after infection, the cells were harvested, washed once with PBS, and pelleted by centrifugation at 5,000 rpm. The pellets were lysed in 1×SDS-PAGE loading buffer at a final concentration of ~1 mg/ml. After boiling for 5 min, 20 $\mu$l of each sample were loaded onto 10% SDS-PAGE gels and simultaneously electrophoresed at 80 V until the dye reached the bottom of the gel. Uninfected Sf9 cells were treated the same as infected cells and used as a negative control. Separated proteins were electrically transferred onto nitrocellulose membrane, blocked with bovine serum albumin, the blots separated into four panels and probed separately with nickel activated HRP conjugate prepared as in Example II, and a commercially available HRP probe activated with nickel via a tetradentate chelator. Probing with the Example II conjugate involved a post-block wash with TBST (25 mM ⁻Tris, 0.15 M NaCl, pH 7.6, 0.05% Tween 20), a 1 hour room temperature incubation with probe diluted in TBST, post-probe wash with TBST, and development of signal on X-ray film using SuperSignal® Substrate from Pierce Chemical Company. Probing with the nickel-activated tetradentate was done according to manufacturer's guidelines for use.

Using the HRP nickel probe of the present invention, the three histidine tagged proteins were detected with high specificity and low background with only small amounts of proteolytic degradations of target fusion protein being detected. With the tetradentate probe, high background and non-specific binding is observed and, compared with the probe of the present invention there is less staining intensity for the target molecule.

EXAMPLE IV

This Example illustrates the preparation of a precursor and its subsequent activation with nickel wherein the molecule, R, containing the primary amine group is a gel.

200 ml of commercially available immobilized diaminodipropylamine on Sepharose CL4B gel is washed thoroughly with 0.1 M MES, pH 5.5. The gel cake is resuspended with 67.2 ml 0.1 M MES, pH 5.5. 82.8 ml NTA solution, pH 9.84 (260 mg/ml in 0.1 M MES, pH 5.5) is added to 50 ml of EDC solution (300 mg/ml in 0.1 M MES, pH 5.5), mixed, and immediately added to the gel slurry with mixing. The gel is allowed to react for 1 hour at room temperature, after which it is drained and washed with 0.1 M MES, pH 5.5. The gel is then activated with nickel by the flow-through addition 6×1 ml aliquots of nickel solution (4 mg nickel ammonium sulfate hexahydrate/ml of water), followed by 3×5 ml washes with TBS (Tris Buffered Saline) to remove excess nickel.

EXAMPLE V

This Example illustrates the comparative binding affinity of the nickel conjugate prepared in Example IV with other nickel-activated gels.

Columns containing three different nickel-activated gels were prepared and tested for relative binding affinity for a non-polyhistidine tagged target molecule. The gel prepared in Example IV described previously was used along with iminodiacetic acid (Pierce Chemical Company) immobilized on Sepharose CL4B (IDA) and a commercially available immobilized nickel-activated tetradentate gel (Tetradentate NTA). The gels were packed into polystyrene columns with 1.5 ml settled gel and washed with Tris buffered saline (TBS, 25 mM Tris, 0.15 M NaCl, pH 7.2). The immobilized iminodiacetic acid gel was activated with nickel by flow through addition of 6×1 ml aliquots of the nickel solution previously described, followed by 3×5 ml washes with TBS to remove excess nickel. The tetradentate gel was pre-activated with nickel as obtained. One ml of mouse IgG, whole molecule (Pierce, 1.5 mg/ml an TBS) was applied to each of the columns and 1 ml fractions were collected as the columns were washed with TBS and then with elution buffer consisting of 50 mM imidazole in TBS. All gels were run simultaneously. Fractions were monitored for protein content at 595 nm following color development with a commercial Coomassie protein assay reagent.

Figure 3:
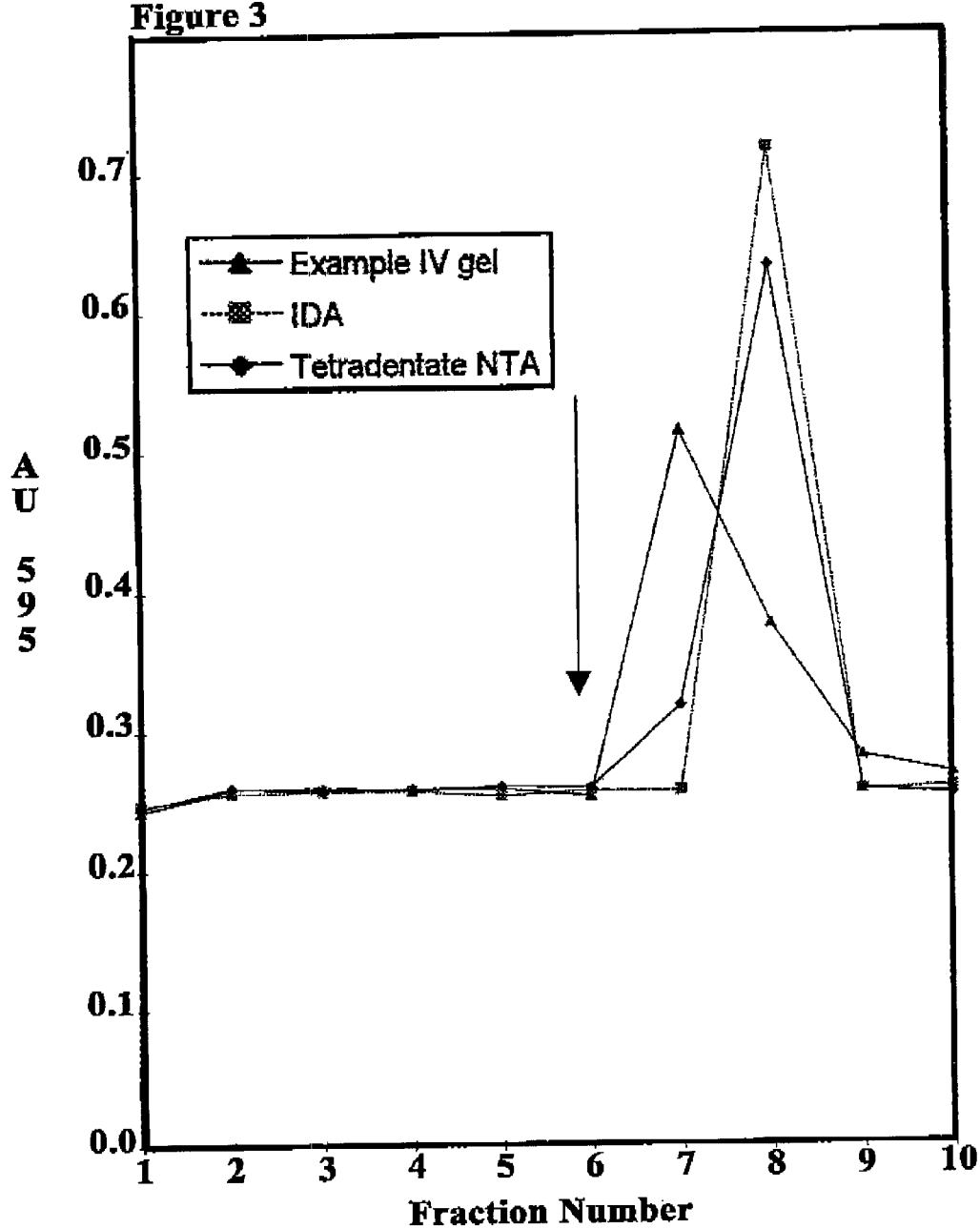
FIG. 3. illustrates elution characteristics of mouse IgG on nickel-activated gel. Arrow indicates addition of elution buffer.

The results are shown in FIG. 3. As shown, the nickel-activated gel of the instant invention (Example IV) exhibited weaker interaction for binding non-polyhistidine tagged material as compared to the other gels (IDA and Tetradentate NTA) as evidenced by quicker elution of the protein on the column compared to the other nickel activated gels. This example further distinguishes the character of the metal-activated chelate of the present invention as compared to other known chelates.

EXAMPLE VI

This Example illustrates the use of the nickel-activated gel prepared in Example IV for the purification of PHT proteins from crude lysates and comparison of non-specific binding with other nickel-activated gels.

3 ml of a PHT fusion protein extract were applied to 1 ml bed volumes of the three different nickel-activated gels described in Example V. Columns were washed with 27 ml of binding buffer (8 M urea, 0.1 M sodium phosphate, 10 mM Tris, pH 8.0), followed by an 18 ml wash with a high stringency wash buffer (8 M urea, 0.1 M sodium phosphate, 10 mM Tris, pH 6.3), and finally washed with 18 ml of a total elution buffer (8 M urea, 0.1 M sodium phosphate, 10 mM Tris, 0.2 M imidazole, pH 6.3). Three ml fractions were collected throughout. The initial column break through fraction, the fraction eluting as a result of the high stringency wash, and the fraction eluting as a result from the total elution buffer, from each column, were concentrated with MilliPore Microcon®-10 microcentrators, diluted to equivalent protein concentrations (as shown by Coomassie Plus Protein Assay Reagent) in 8 M urea, and run on a polyacrylamide gel. Fractions were concentrated and equivalent amounts of protein (4.8 µg) from peak fractions were run on a 4–20% gradient polyacrylamide electrophoresis gel run under denaturing conditions followed by Coomassie blue staining. Fraction 11 identifies the first fraction resulting from the high stringency wash; fraction 17 identifies the total elution fraction. Comparison of the fraction 11 and 17 profiles among the gel types demonstrated that the nickel-activated chelate gel of the present invention was more specific for binding the PHT fusion protein; there being substantial amounts of contaminating non-target molecules being retained on the other nickel-activated gels.

The following Examples VII–XI illustrate the application of the above described precursor and metal chelate conjugate formed therefrom in the preparation of an acceptor surface which includes a solid phase, in these cases a polystyrene microtiter plate, having the precursor or conjugate noncovalently adhered thereto wherein the molecule R is a protein. The illustrated modifications that are introduced onto the proteins (cationization, chelating moiety) serve to provide the means for modulating (decreasing or increasing) the acceptance of the illustrated foreign substances, in these cases an affinity probe (decreased affinity) or PHT fusion proteins (increased affinity), to the surface of the polystyrene.

EXAMPLE VII

This Example illustrates the preparation of a precursor in accordance with the present invention where the molecule, R, containing the primary amine group is cationized bovine serum albumin (cBSA), the non-covalent immobilization of this precursor onto the solid phase, a polystyrene plate, to provide an acceptor surface with nickel activation; the acceptor surface thus being prepared to selectively bind PHT fusion proteins.

112 mg cBSA (commercially available from Pierce Chemical Company) was dissolved with 6.216 ml 0.1 M MES, pH 5.5. To this solution, 2.258 ml NTA solution, pH 9.84 (260 mg/ml in 0.1 M MES, pH 5.5) was added, followed by addition of 2.727 ml EDC solution (150 mg/ml in 0.1 M MES, pH 5.5). This solution was mixed and allowed to react for 2 hours at room temperature. After reaction, the solution was diluted with 0.1 M MES, pH 5.5 (1 volume reaction mix plus 19 volumes buffer), and added to flat-bottom transparent polystyrene strip plates at 200 µl/well. The solution was allowed to coat the plates for 2 hours at room temperature, and then was washed 3×200 µl with 0.1 M MES, pH 5.5. After air drying, plates were activated with nickel by addition of 200 µl nickel solution (4 mg nickel ammonium sulfate hexahydrate per ml water). (Similar results are attainable with nickel activation carried out immediately on the surface without the optional air drying step.) After incubation for 30 minutes at room temperature, wells were washed 3×200 µl with water and allowed to air dry. Alternatively, similar results could be obtained with plates where the cBSA could be first bound to the plate, followed by the EDC reaction with NTA, and subsequently activated with nickel.

EXAMPLE VIII

This Example illustrates the use of nickel-activated chelate plates prepared in Example VII for capture of PHT fusion proteins and demonstration of nickel dependency. As shown in this Example, the solid polystyrene phase has been modulated to increase its interaction with the foreign substance, in this case a PHT fusion protein. The surface has therefore been prepared to increase the interaction in a selective fashion for PHT fusion proteins by the use of the divalent nickel ion.

Figure 4:
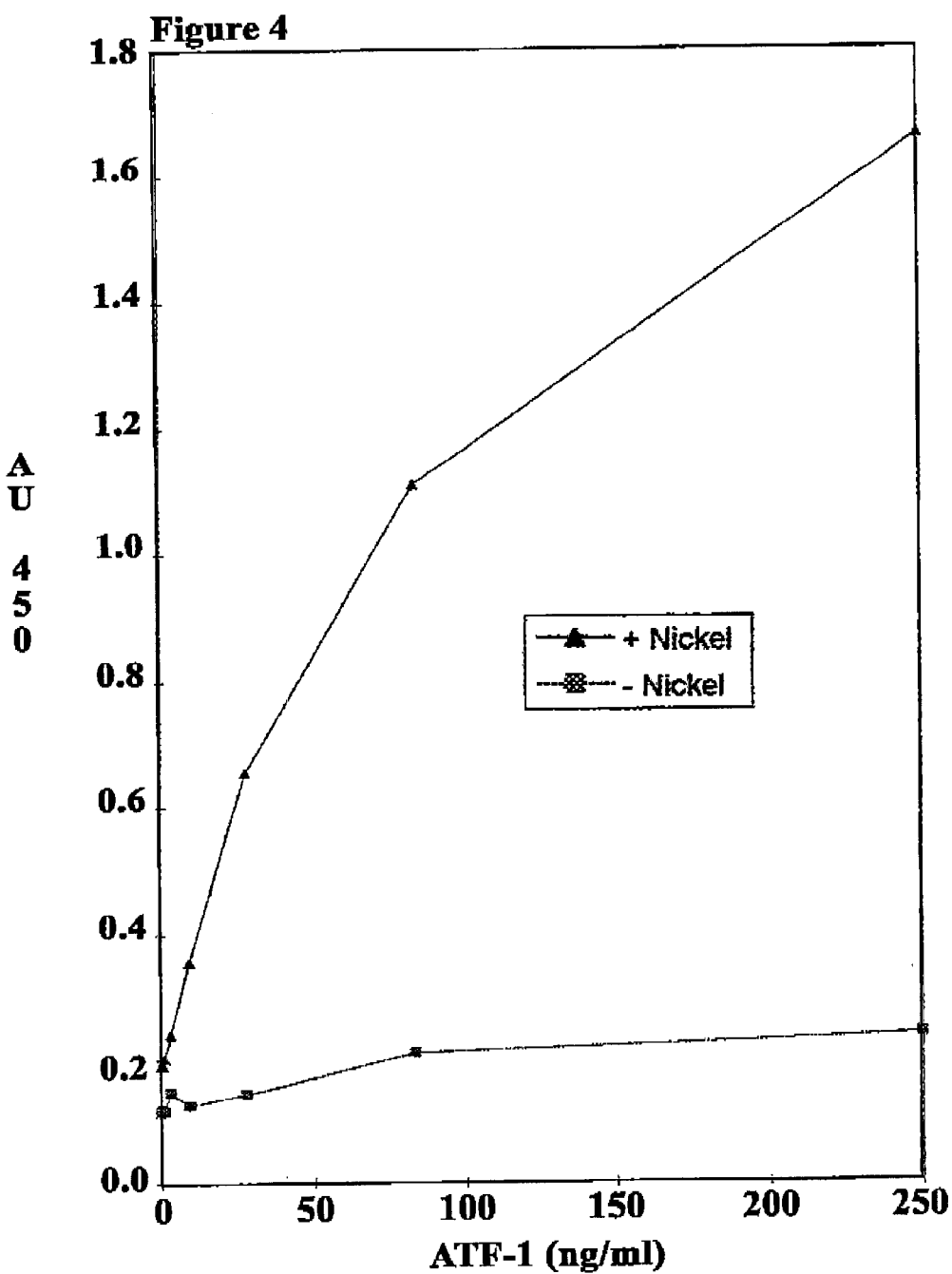
FIG. 4. shows an absorbance profile resulting, from the use of chelate plates activated or not activated with nickel in a PHT fusion protein assay.

Serial dilutions of the polyhistidine tagged fusion protein ATF-1 (Santa Cruz) were prepared in PBS (phosphate buffered saline). 100 µl of each dilution was added to the wells of nickel activated plates or non-nickel activated plates (nickel addition omitted) and allow to incubate for 1 hour at room temperature with shaking. After binding to the plate, wells were washed 3×200 µl with PBS/Tween (0.1 M sodium phosphate, 0.15 M NaCl, pH 7.2, 0.05% Tween 20). Commercially available mouse monoclonal anti ATF-1 primary antibody was diluted 1:1000 in PBS and then added at 100 µl to the wells. After incubation for 1 hour at room temperature with shaking, the primary antibody was decanted and wells were washed 3×200 μl with PBS/Tween. 100 μl of secondary polyclonal antibody (goat anti-mouse IgG, HRP conjugate, Pierce diluted 1:5000 with PBS) was then added and allowed to bind for 1 hour at room temperature with shaking. Wells were decanted and washed 3×200 μl with PBS/Tween. Color was developed with 100 μl Turbo-TMB ELISA (Pierce Chemical Company) followed by stopping with 100 μl 1 N sulfuric acid. Absorbance developed from the wells was quantitated at 450 nm. Results are shown in FIG. 4. As shown, the polyhistidine tagged fusion protein was captured by the nickel-activated metal chelate and binding was dependent on nickel activation of the plate.

EXAMPLE IX

The following Example illustrates the use of a preformed chemically modified protein, in this case cBSA, for noncovalent immobilization to a solid phase for the purpose of modulating subsequent interactions with the foreign substances, in this case the precursor of Example I or iron-activated precursor of Example II. As shown in this example, an acceptor surface has been prepared to decrease its interaction with the foreign substance.

Figure 5:
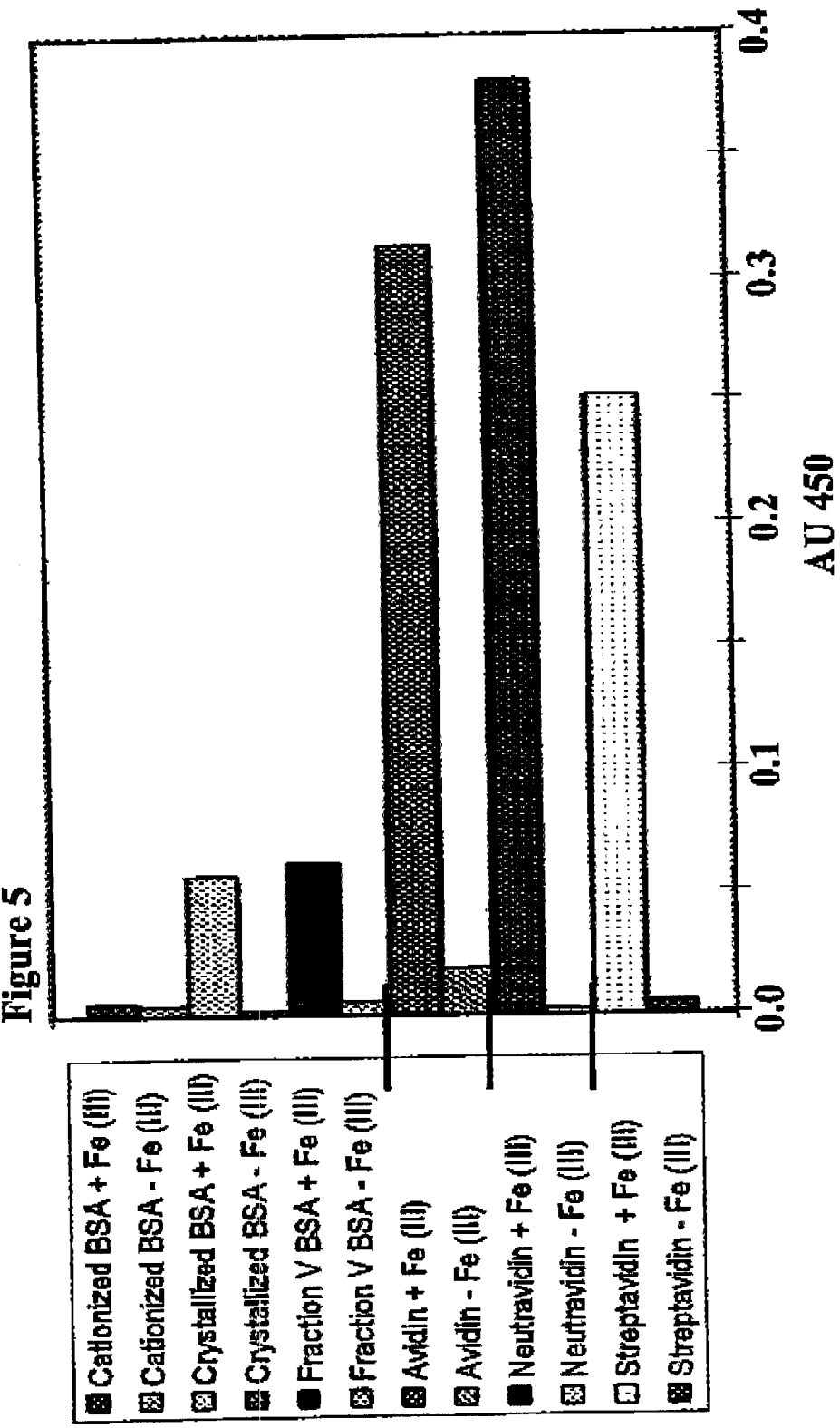
FIG. 5. depicts the iron dependency of the precursor for binding to various proteins. The iron-activated precursor bound to all proteins except for the protein that had been chemically modified.

A variety of non-phosphorylated proteins were coated onto polystyrene microtiter plate wells and the binding activity of the precursor of Example I and the iron-activated conjugate of Example II was determined. These proteins included a variety of native proteins and a chemically modified protein, cBSA. Proteins were coated onto wells at 2 mg protein/ml and were allowed to bind to wells with overnight shaking at room temperature to ensure complete binding to the well surface. Following coating, wells were washed 4×200 μl with 0.1 M sodium acetate, pH 5.0, followed by a 2 hour room temperature incubation with the precursor and conjugate (4 μg/ml in 0.1 M sodium acetate, pH 5.0). The wells were then washed 4×200 μl with 0.1 M sodium acetate, pH 5.0, followed by color development with 100 μl Turbo TMB ELISA and subsequent stopping with 100 μl 1 N phosphoric acid. Absorbance developed from the wells was quantitated at 450 nm. Results are shown in FIG. 5. As can be seen, iron activation of the conjugate resulted in high levels of binding to bovine serum albumin (BSA, fraction V or crystallized grade), avidin, neutravidin, and streptavidin. Without iron activation of the precursor, binding to these proteins was negligible. No binding of the conjugate or precursor was observed to the chemically modified protein cationized BSA (cBSA). Therefore, chemically modified proteins are useful for modulating the interaction with foreign substances in a negative fashion as shown by the inability of the conjugate to bind to cBSA.

EXAMPLE X

The following Example illustrates the preparation of an acceptor surface by chemically modification of a preformed solid-phase surfaces for the purpose of modulating subsequent interactions with foreign substances. As shown in this example, the constructed solid phase surface has been modulated in a fashion to decrease its interaction with a foreign substance, in this case the iron-charged metal chelate of peroxidase.

A Neutravidin Coated Microtiter Polystyrene Strip Plate (Pierce Chemical Company) was chemically modified for various times using ethylenediamine/EDC. Subsequently, the reactivity of the chemically modified surface was monitored by incubation with the iron-activated conjugate of Example II.

Figure 6:
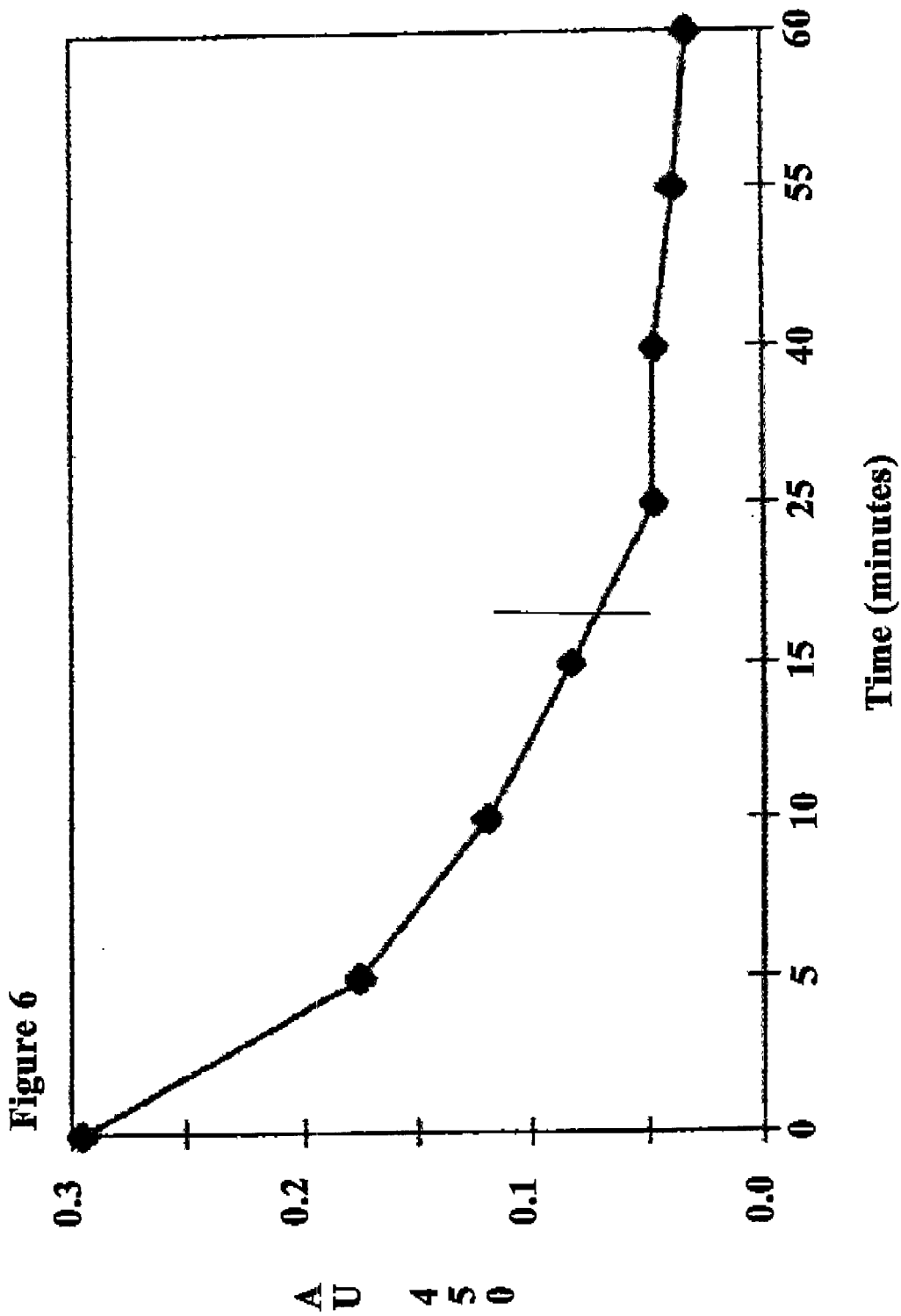
FIG. 6. depicts the modification of a preformed solid phase surface by chemical modification to modulate the binding characteristics of a foreign substance. Increasing the time of chemical modification decreased the interaction of the foreign substance with the surface.

A solution consisting of 50 mM ethylenediamine.HCl, 25 mM EDC, 0.1 M MES, pH 5.0 was added at 100 μl per well and incubated with the wells for 60, 55, 40, 25, 15, 10, and 5 minutes. Separate wells received no solution addition to serve as a control. Following reaction with the well surface, wells were decanted and washed 3×200 μl with 50 mM ethylenediamine.HCl, 0.1 M MES, pH 5.0, followed by 3×200 μl washes with 0.1 M sodium acetate, 1.0 M NaCl, pH 5.0. The iron activated HRP chelated was incubated with the wells at 4 μg/ml in 0.1 M sodium acetate, 1.0 M NaCl, pH 5.0, 0.5 mg cBSA/ml, 0.05% Tween 20. Following binding, wells were decanted and washed 5×200 μl with 0.1 M sodium acetate, 1.0 M NaCl, pH 5.0. Color was developed with 100 μl Turbo TMB ELISA followed by stopping with 100 μl 1 N sulfuric acid. Absorbance developed from the wells was quantitated at 450 nm. Results are shown in FIG. 6. The binding of the surface was modulated for the iron conjugate in a time-dependent fashion; the interaction decreased with increasing time of chemical modification.

EXAMPLE XI

The following example illustrates the preparation of an acceptor surface by chemical modification of a preformed surface for the purpose of modulating subsequent interactions with foreign substances, in conjunction with the use of the iron conjugate of Example II to allow for phosphate detection by the conjugate. As shown in this example, chemical modification of the preformed surface allows for the iron conjugate to exhibit complete specificity for the detection of a phosphate-containing target molecule.

Figure 7A:
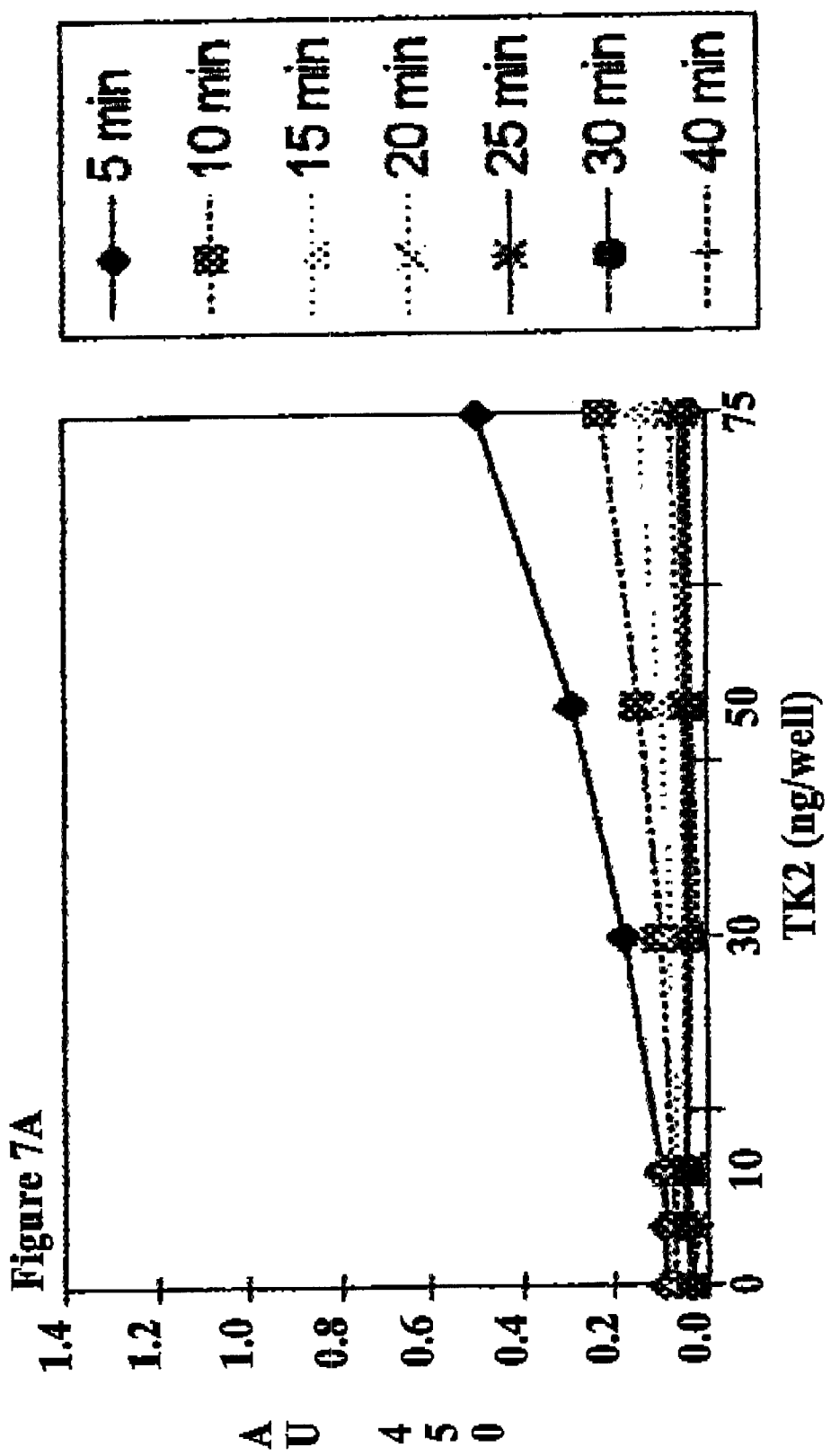
FIGS. 7A., 73B., 7C. depict the assay performance of an iron-activated conjugate or phosphate and nonphosphate-containing target molecules in conjunction with chemical modification of the preformed surfaces containing the target molecules.
Figure 7B:
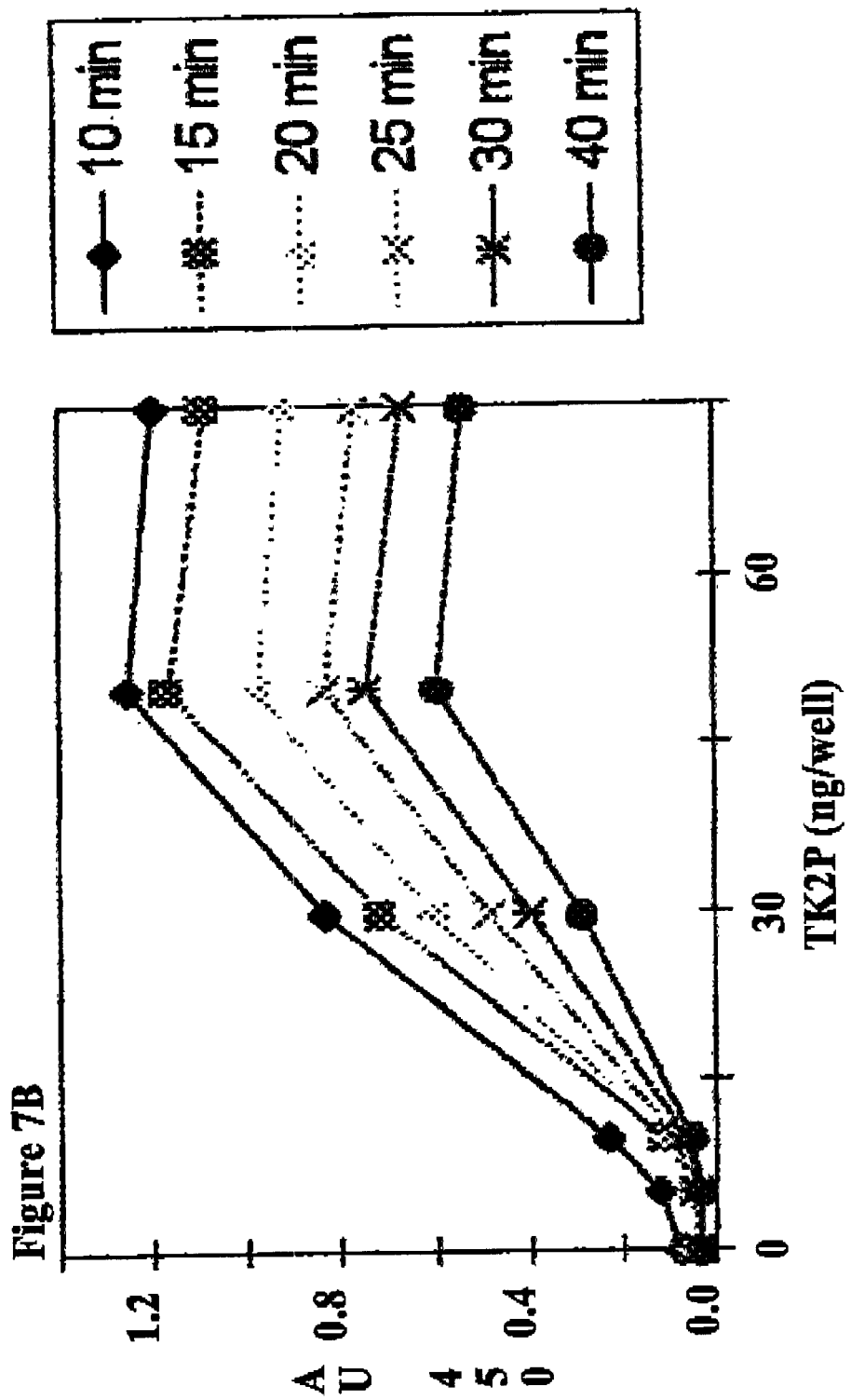
Figure 7C:
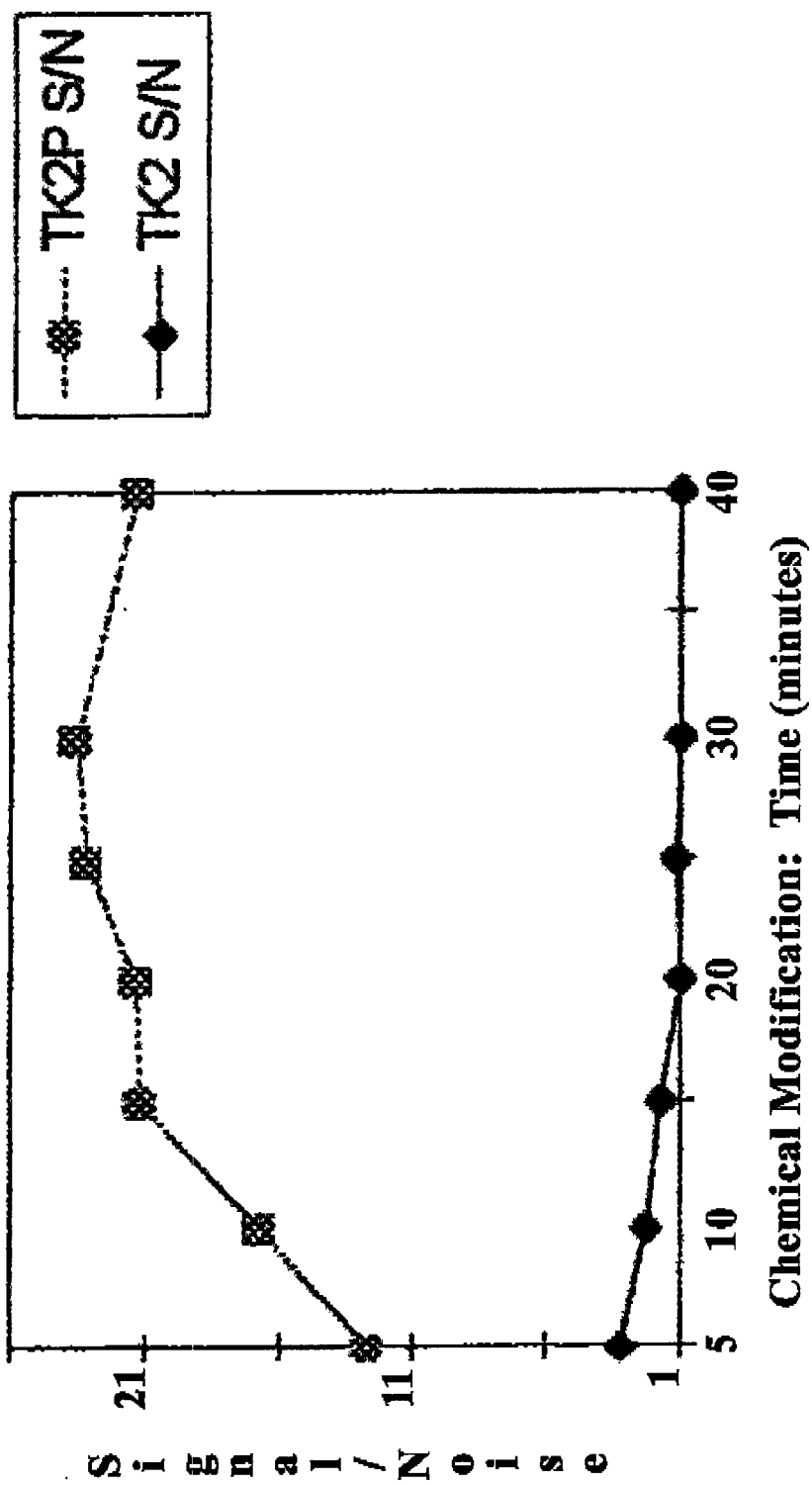

Biotinylated Tyrosine kinase peptide in the nonphosphorylated form (TK2) and phosphorylated form (TK2P) were diluted to give 0.75, 0.5, 0.3, 0.1, 0.05, and 0 μg/ml in 0.1 M sodium acetate, pH 5.0, and bound to Neutravidin Coated Polystyrene Strip Plates (Pierce Chemical Company) for 2 hours at room temperature with shaking. After binding, wells were decanted and washed with 3×200 μl 0.1 M sodium acetate, 1.0 M NaCl, pH 5.0, followed by 3×200 μl washes with 0.1 M MES, pH 5.0. Each concentration series of the bound peptide pairs was subjected to chemical modification consisting of reaction with 200 μl 0.1 MES, pH 5.0, 50 mM ethylenediamine.HCl, 25 mM EDC, for various times. Following chemical modification, wells were washed 3×200 μl with 0.1 M MES, pH 5.0, 50 mM ethylenediamine.HCl, and then 3×200 μl with 0.1 M sodium acetate, 1.0 M NaCl, pH 5.0. Wells were then incubated for 1 hour with the 100 μl iron activated conjugate of Example II at 4 μg/ml in 0.1 M sodium acetate, 1.0 M NaCl, pH 5.0, 0.05% Tween 20. After washing 5×200 μl with 0.1 M sodium acetate, 1.0 M NaCl, pH 5.0, color was developed with 100 μl Turbo TMB ELISA followed by stopping with 100 μl 1 N sulfuric acid. Absorbance developed from the wells was quantitated at 450 nm. Results are shown in FIGS. 7A, 7B, and 7C. When the tyrosine kinase peptide in either the phosphorylated or nonphosphorylated form was bound to Neutravidin coated microtiter plates, both species could be detected. However, the plates surfaces could be chemically modified after peptide binding, and therefore allow the iron-activated conjugate to be entirely specific for the phosphate group. This treatment had a time dependent effect on decreasing background and improving the signal/noise ratios obtainable in the assay (FIG. 7C). A variety of other phosphate-containing molecules can be detected in similar specific fashion, including phosphoserine and phosphothreonine.

While Examples VII–XI have illustrated the preparation of an acceptor surface with specific reference to the surface being polystyrene and the chemically modified protein being cBSA or the precursor set forth in Example I or metal ion conjugates thereof, other solid phases and chemically modified proteins can also be constructed. Other solid phases capable of immobilizing proteins in a noncovalent manner are considered useful. Examples include polyvinyl chloride, nitrocellulose, nylon, glass, and other materials useful for microtiter plate construction. Other proteins capable of noncovalently binding to solid phases, in addition to those specifically identified, which are capable of chemically modification to permit modulation of acceptor molecules can also be used to prepare acceptor surfaces on a solid phase. Examples include IgG, neutravidin, and ovalbumin. Chemical modifications other than those specifically illustrated that are considered useful include incorporation of a variety of functionalities, including biotin, N-hydroxysuccinimide esters, maleimide groups, glutathione, isothiocyanates, fluorescein, polyhistidine, etc.

What is claimed is:

1. A method of preparing a composition for chelating multivalent ions consisting essentially of a monomeric form of a conjugate having the structure:

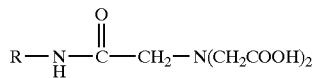

wherein R is a proteinaceous molecule, the method comprising reacting nitrilotriacetic acid or a salt thereof in an aqueous medium at alkaline pH of at least 8 with a proteinaceous molecule containing a primary amine group in the presence of a carbodiimide.

2. The method of claim 1 wherein the proteinaceous molecule is an enzyme.

3. The method of claim 2 wherein the enzyme is alkaline phosphatase.

4. The method of claim 2 wherein the enzyme is horseradish peroxidase.

5. The method of claim 1 wherein the proteinaceous molecule is bovine serum albumin.

6. The method of claim 1 including the step of chelating the composition so prepared to a multivalent nickel ion.

7. The method of claim 1 including the step of chelating the composition so prepared to a multivalent iron ion.

8. The method of claim 1 including the step of chelating the composition so prepared to a multivalent copper ion.

9. The composition for chelating multivalent metal ions prepared by the method of claim 1.

10. The composition for chelating multivalent metal ions prepared by the method of claim 2.

11. The composition for chelating multivalent metal ions prepared by the method of claim 3.

12. The composition for chelating multivalent metal ions prepared by the method of claim 4.

13. The composition for chelating multivalent metal ions prepared by the method of claim 5.

14. An acceptor surface comprising a solid phase having non-covalently adhered thereto the composition for chelating multivalent metal ions prepared by the method of claim 1.

15. The acceptor surface of claim 14 wherein the solid phase is polystyrene.

* * * * *